(12) United States Patent  
Feigenwinter et al.

(10) Patent No.: US 7,883,544 B2
(45) Date of Patent: *Feb. 8, 2011

(54) CONDYLAR HEAD ADD-ON SYSTEM

(75) Inventors: Gregor Feigenwinter, Lampenberg (CH); Andre Furrer, Luterkofen (CH)

(73) Assignee: Sythes USA, LLC, West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/576,476

(22) Filed: Oct. 9, 2009

(65) Prior Publication Data

US 2010/0030214 A1    Feb. 4, 2010

Related U.S. Application Data

(63) Continuation of application No. 11/376,469, filed on Mar. 14, 2006, now Pat. No. 7,601,175.

(51) Int. Cl.
A61F 2/02 (2006.01)

(52) U.S. Cl. .................. 623/17.17; 623/17.18

(58) Field of Classification Search ........... 623/17.17
See application file for complete search history.

(56) References Cited

U.S. PATENT DOCUMENTS

| 3,720,959 | A | * | 3/1973 | Hahn | 623/17.17 |
| 4,693,722 | A | * | 9/1987 | Wall | 623/17.17 |
| 5,989,292 | A | * | 11/1999 | van Loon | 623/17.17 |
| 2005/0234452 | A1 | * | 10/2005 | Malandain | 606/61 |

* cited by examiner

*Primary Examiner*—Bruce E Snow
*Assistant Examiner*—Melissa Hoban
(74) *Attorney, Agent, or Firm*—Woodcock Washburn LLP

(57) ABSTRACT

The present invention generally relates to mandibular prostheses. More particularly, the invention relates to a condylar-head replacement for reconstruction of the temporomandibular joint after resection of the condyloid process. The present invention provides a condylar-head replacement comprising a condylar-head attachment that may be adjustably positioned on a reconstruction plate to achieve various condylar-head heights. The condylar-head height adjustment allows the condylar-head replacement to be fit to a particular patient. The condylar-head replacement of the present invention obviates the need for custom fabrication of a condylar-head replacement for a patient.

23 Claims, 9 Drawing Sheets

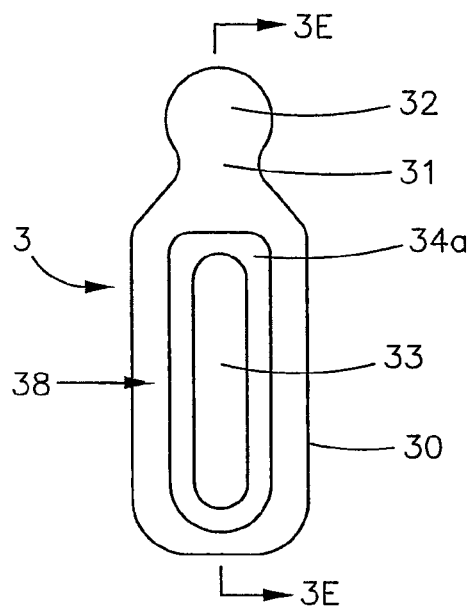
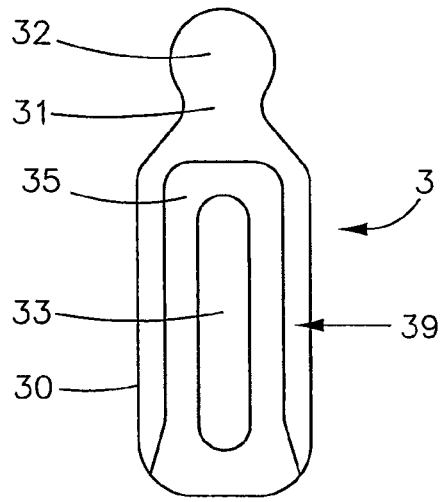
Fig. 3A  Fig. 3B
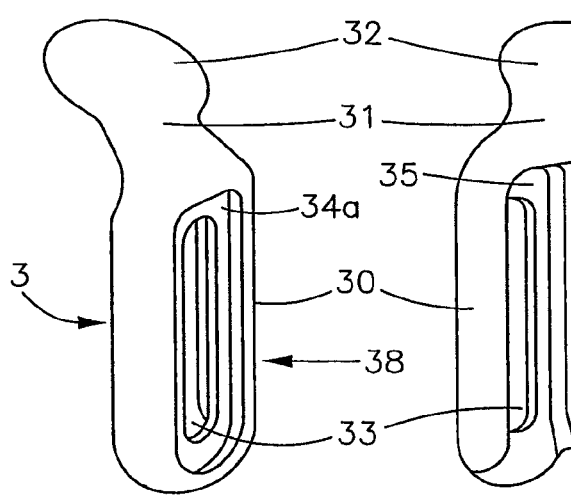
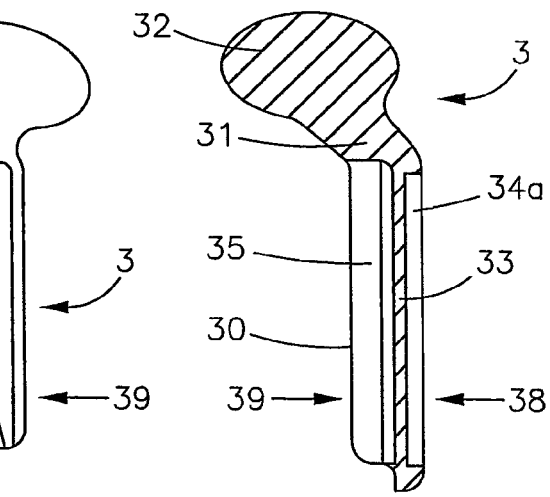
Fig. 3C  Fig. 3D  Fig. 3E

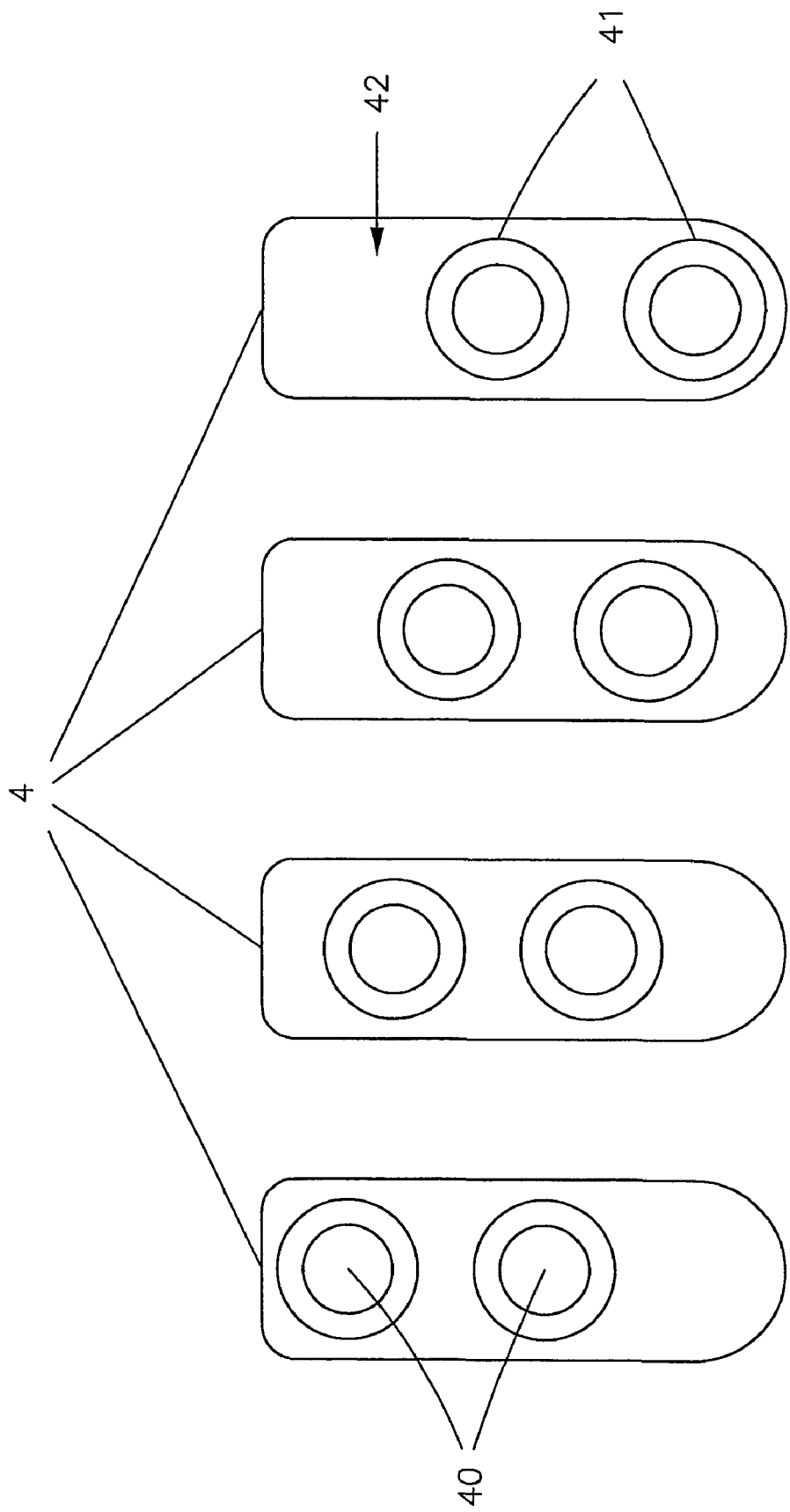

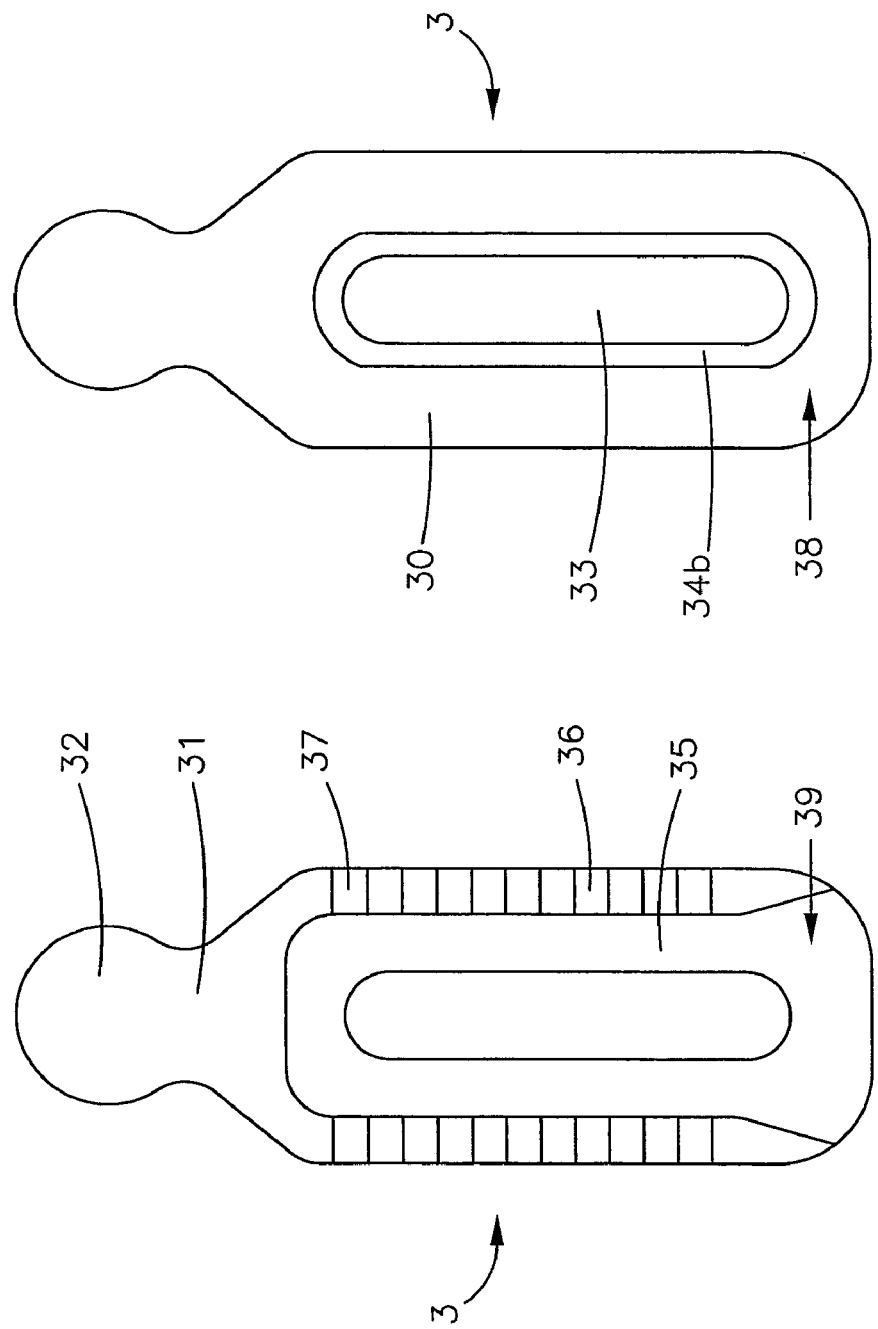

CONDYLAR HEAD ADD-ON SYSTEM

CROSS REFERENCE TO RELATED APPLICATION

This application is a Continuation Application of U.S. patent application Ser. No. 11/376,469, filed Mar. 14, 2006, the disclosure of which is incorporated herein by reference in its entirety.

TECHNICAL FIELD

The present invention generally relates to the field of mandibular prostheses. More particularly, the invention relates to an improved condylar-head replacement for the mandibular condyle.

BACKGROUND

The mandible consists of a horizontal, horse-shoe shaped portion having an upwardly and rearwardly extending posterior portion on each end. The upwardly and rearwardly extending posterior portions are called rami (ramus singular). The upper end of each ramus terminates in a forward coronoid process and a rearward condyloid process. The condyloid process consists of two portions—the condyle and its supporting structure, the neck. The condyle is a convex, knob-shaped protrusion that fits into a concave, cup-shaped socket in the temporal bone of the skull, called the glenoid fossa. The mandibular condyle and the glenoid fossa form the temporo-mandibular joint that allows the free movement of the lower jaw.

Disease or injury to the mandible may require resection of the condyloid process. After resection of the condyloid process, it is necessary to implant a prosthesis to span the missing segment of the mandible. When implanting a prosthetic condyloid process, it is important to provide a proper fit between the prosthetic condyle and the glenoid fossa. In other words, it is important to provide a proper condylar-head height on the ramus. Otherwise, the normal relationship between the condyle and glenoid fossa may be disturbed, resulting in disruption of the normal jaw function, or alteration of the occlusion or bite. Such a disruption may result in discomfort for the patient. Even in cases where it is only necessary to provide a temporary implant until a definitive reconstructive procedure can be performed, it is still important to provide a proper fit between the prosthetic condyle and the glenoid fossa to avoid unnecessary discomfort for the patient.

SUMMARY

The invention provides a condylar-head replacement for reconstruction of the mandible after resection of the condyloid process. According to one embodiment of the invention, the condylar-head replacement comprises a condylar-head attachment that may be secured on a mandibular reconstruction plate and that may be adjusted to achieve various condylar-head heights. The height adjustment of the condylar-head attachment allows the condylar-head replacement to be fit on a plurality of patients.

According to one embodiment of the invention, the condylar-head attachment comprises a primary attachment plate having a condylar head attached to the top by a neck. Preferably, the primary attachment plate further comprises a slot substantially in the center and a recess extending outwardly from and circumferentially around the slot.

According to another embodiment of the invention, the condylar-head replacement may further comprise a height-adjustment plate. In this embodiment, a height-adjustment plate, corresponding to a specific condylar-head height, is placed over the slot of the primary attachment plate so that it rests in the recess of the primary attachment plate. The height-adjustment plate has at least one screw hole that aligns over the slot of the primary attachment plate. Preferably, the height-adjustment plate may be selected from a variety of height-adjustment plates having screw holes in different positions corresponding to different condylar-head heights.

According to another aspect of the invention, the combination of the primary attachment plate and height-adjustment plate is placed over the reconstruction plate with the height-adjustment plate preferably placed over the lateral side of the reconstruction plate such that the holes in the height-adjustment plate align with holes in the reconstruction plate. Accordingly, the condylar-head attachment may be secured to a reconstruction plate at a desired height by selecting a corresponding height-adjustment plate. Preferably, the condylar-head attachment is secured to the reconstruction plate using fasteners, such as screws, which may pass through the holes in the height-adjustment plate and into the holes in the reconstruction plate.

In another embodiment of the invention, the height adjustment of the condylar-head attachment does not require the use of a height-adjustment plate. The condylar-head attachment may be secured directly to the reconstruction plate while still allowing height adjustment of the condylar-head attachment. In this embodiment, the primary attachment plate may be positioned over a lateral side of the reconstruction plate at a desired height, such that the slot on the primary attachment plate is aligned with the holes on the reconstruction plate. The slot on the primary attachment plate allows the condylar-head attachment to be secured to a reconstruction plate at various heights. Preferably, fasteners, such as screws, pass through the slot in the primary attachment plate and into holes in the reconstruction plate. The heads of fasteners engage the attachment plate and the recess surrounding the slot may act as a countersink for the heads.

According to another embodiment, the condylar-head attachment may further comprise a series of tenons and mortises disposed on a medial side of the primary attachment plate, adjacent to the longitudinal edges of the slot. Further, according to this embodiment, the condylar-head attachment may comprise a secondary attachment plate. Preferably, the secondary attachment plate has a recessed channel along a longitudinal midline, at least one hole in the recessed channel along the same longitudinal midline, and a series of mortises and tenons on a lateral side adjacent to the longitudinal edges of the recessed channel. The mortises and tenons on the secondary attachment plate complement the mortises and tenons on the primary attachment plate.

Preferably, in this embodiment, a reconstruction plate is disposed in the recessed channel of the secondary attachment plate; and the holes of the secondary attachment plate are aligned with holes on the reconstruction plate. The primary attachment plate may be positioned over the reconstruction plate such that the slot on the primary attachment plate is aligned with holes on the reconstruction plate, and the medial side of the primary attachment plate engages the lateral side of the secondary attachment plate. In this embodiment, the primary attachment plate engages the secondary attachment plate by mating of the complementary and opposing mortises and tenons.

Preferably, in this embodiment, fasteners, such as bolts, are put through the secondary attachment plate and into the holes in the reconstruction plate. The fasteners preferably have hollow center cavities that extend into openings at the tips of the fasteners. Further, fasteners, such as screws, may be used to secure the primary attachment plate to the reconstruction plate by passing the fasteners through the slot and into the center cavities of the bolts that secure the secondary attachment plate to the reconstruction plate. Alternatively, in this embodiment, the secondary attachment plate and the primary attachment plate may be secured to a reconstruction plate without the use of the bolts. For example, the secondary attachment plate may be disposed on one side of a reconstruction plate; the primary attachment plate may be disposed on an opposite side of the reconstruction plate; and screws may be passed through the primary attachment plate, through the reconstruction plate, and into the secondary attachment plate, or vice versa.

According to another aspect of the invention, the condylar-head replacement may be used as a temporary implant after resection of the mandibular condyle until a definitive and more permanent reconstructive procedure can be performed. Alternatively, the condylar-head replacement of the present invention may be used as a permanent prosthesis for permanent reconstruction of the condyloid process.

Additional features and advantages of the invention will be made apparent from the following detailed description of illustrative embodiments that proceeds with reference to the accompanying drawings.

BRIEF DESCRIPTION OF THE DRAWINGS

The foregoing summary, as well as the following detailed description of the preferred embodiments, is better understood when read in conjunction with the appended drawings. For the purpose of illustrating the invention, there is shown in the drawings embodiments that are presently preferred, it being understood, however, that the invention is not limited to the specific methods and instrumentalities disclosed. In the drawings:

FIG. 3A shows a view of the lateral side of an exemplary condylar-head attachment;

FIG. 3B shows a view of the medial side of the exemplary condylar-head attachment of FIG. 3A;

FIG. 3C shows a perspective view of the lateral side of the exemplary condylar-head attachment of FIG. 3A;

FIG. 3D shows a perspective view of the medial side of the exemplary condylar-head attachment of FIG. 3B;

FIG. 3E shows a cross-sectional view of the exemplary condylar-head attachment of FIG. 3A, taken along section line 3E-3E in FIG. 3A;

FIGS. 4A-4D show a set of exemplary height-adjustment plates;

FIG. 8A shows a view of the medial side of the exemplary condylar-head attachment in FIGS. 7A-7D;

FIG. 8B shows a view of the lateral side of the exemplary condylar-head attachment in FIGS. 7A-7D;

DETAILED DESCRIPTION OF ILLUSTRATIVE EMBODIMENTS

The present invention generally relates to mandibular prostheses. More particularly, the invention relates to a condylar-head replacement 1 for reconstruction of the temporomandibular joint after resection of the condyloid process. The condylar-head replacement 1 of the present invention can be attached to a reconstruction plate 2 at various heights in order to accommodate different patients during reconstruction of the condyloid process. The reconstruction plate may comprise a conventional reconstruction plate.

In order to better describe the invention and the relationship of its various elements, it is necessary to provide a spatial frame of reference. The sagittal plane is an imaginary plane dividing the human body down the midline into a right half and a left half. Medial means closer to the midline, while lateral means further from the midline. The coronal plane is an imaginary plane dividing the human body into a front half and a back half. Anterior means further forward, while posterior means further back. By extension, objects that are placed in the human body, e.g. a condylar-head replacement 1 in accordance with embodiments of this invention, may be described with respect to this frame of reference.

Figure 1:
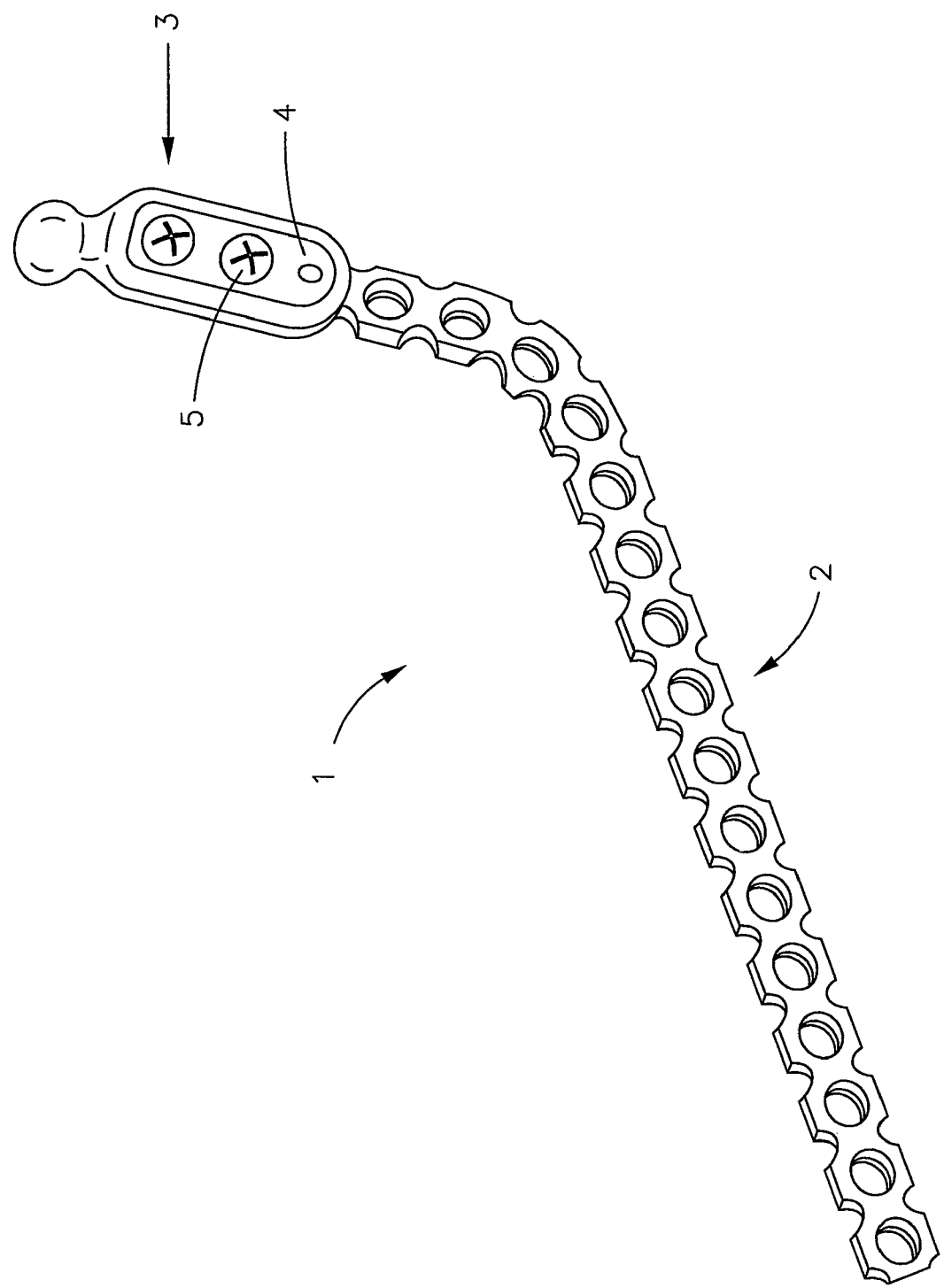
FIG. 1 shows an exemplary condylar-head replacement attached to a reconstruction plate.

FIG. 1, shows a preferred embodiment of the condylar-head replacement 1. As shown in FIG. 1, the condylar-head replacement 1 may include a reconstruction plate 2, a condylar-head attachment 3, a height adjustment plate 4, and screws 5.

Figure 2:
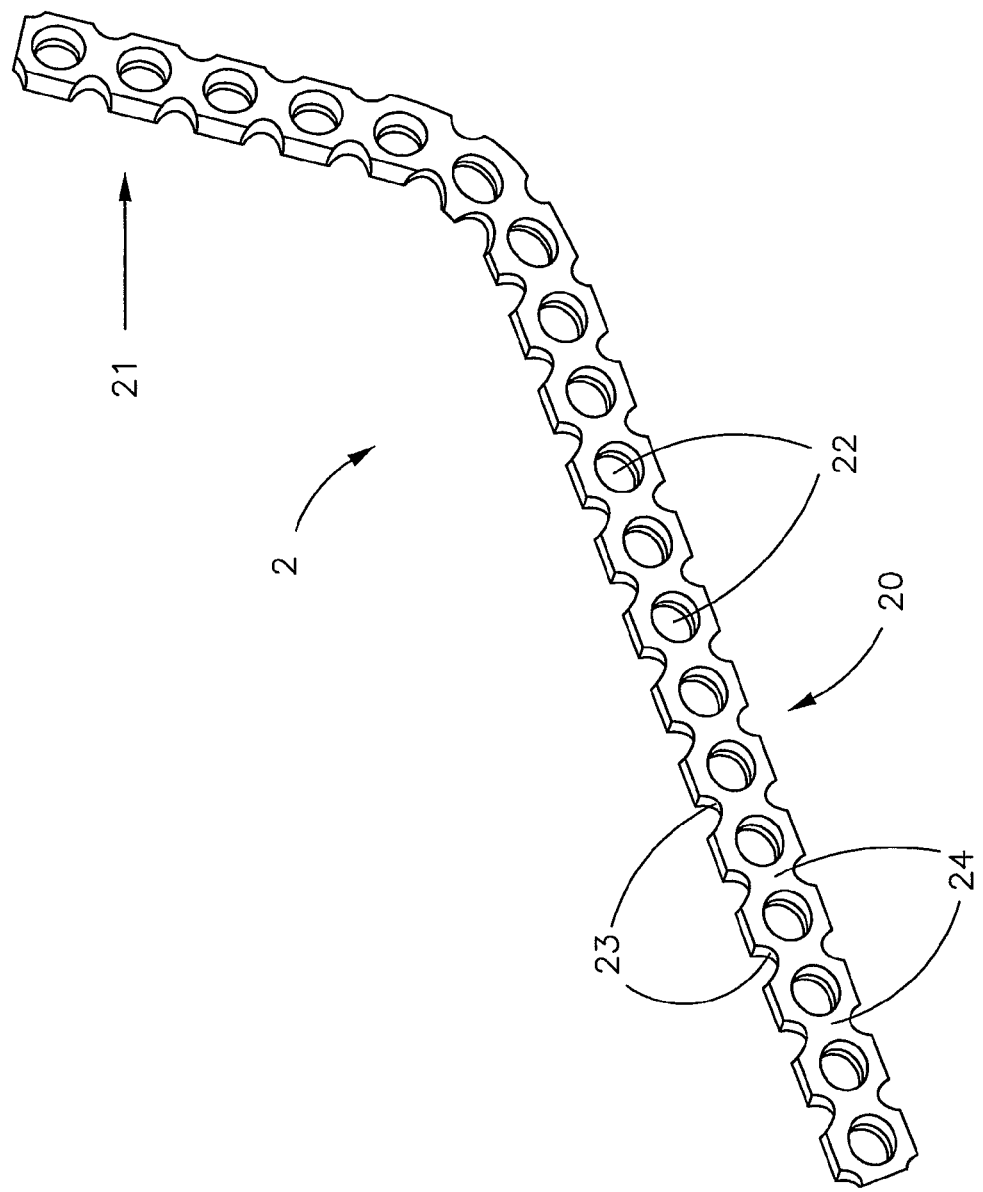
FIG. 2 shows an exemplary reconstruction plate.

FIG. 2 shows an exemplary mandibular reconstruction plate 2. As shown, the reconstruction plate 2 may be shaped substantially like a lateral portion of the mandible, having an anterior portion 20 and a posterior portion 21 that extends upwardly and rearwardly. Also, the conventional reconstruction plate 2 may include a plurality of holes 22 that are evenly spaced apart along its length. As shown, a reconstruction plate 2 may also include a plurality of notches 23 cutout of the top and bottom edges of the plate 2, forming intersection bars 24 between the holes 22.

FIGS. 3A-3E show a preferred embodiment of the condylar-head attachment 3. As shown in FIGS. 3A-3E, the condylar-head attachment 3 includes a primary attachment plate 30, a neck 31, and a condylar head 32. As shown, the condylar head 32 may comprise a convex, knob-shaped protrusion attached to the superior end of the primary attachment plate 30 by a neck 31. Also, a slot 33 may be formed by a cutout in the center of the primary attachment plate 30 along the longitudinal direction. As shown in FIGS. 3A, 3C and 3E, a recess 34a may be formed on the lateral side 38 of the primary attachment plate 30 extending out from and circumferentially around the slot 33. As shown, the recess 34a preferably has a substantially rectangular shape that is asymmetrical along a centerline dividing the top half and the bottom half of the recess 34a. As shown in FIGS. 3B, 3D, and 3E, a recessed channel 35 may be formed on the medial side 39 of the primary attachment plate 30 that extends around the slot 33 from proximate the neck 31 to the bottom of the primary attachment plate 30. Preferably, the recessed channel 35 has an open end at the bottom of the primary attachment plate 30. As shown, the recessed channel 35 may have a substantially rectangular shape.

FIGS. 4A-4D show a set of exemplary height-adjustment plates 4. As shown, a height adjustment plate 4 may have a substantially rectangular shape that is asymmetrical along a centerline dividing the top half and the bottom half of the plate 4. Further, there are preferably two holes 40 aligned along a longitudinal midline of the height-adjustment plate. The height-adjustment plate 4 may also include countersinks 41, formed concentrically around the holes 40 on the lateral side 42 of the plate 4. Preferably, the holes 40 are spaced apart substantially the same distance as the holes 22 in a complementary reconstruction plate 2. As shown, the holes 40 in the height-adjustment plate 4 may be placed in different positions along the longitudinal midline of the plate 4. A particular placement of the holes on the height-adjustment plate 4 corresponds to a particular condylar-head height. According to a preferred embodiment, the height-adjustment plate 4 for a particular patient may be selected from a plurality of plates 4 corresponding to different condylar-head heights.

Referring to FIGS. 3A and 4A-4D, a recess 34a and a height-adjustment plate 4 may have complementary asymmetrical shapes so that the height-adjustment plate 4 may be longitudinally oriented in the recess 34a in only one way. Alternatively, as shown in FIG. 5A, a recess 34a and a height-adjustment plate 4 may have complementary symmetrical shapes so that the height-adjustment plate 4 may be longitudinally oriented in the recess 34a in more than one way, whereby the height-adjustment plate 4 may correspond to more than one condylar-head height. For example, a symmetrical height-adjustment plate 4 may correspond to a particular condylar-head height in one position, but may correspond to another condylar-head height when rotated 180 degrees.

Figure 5B:
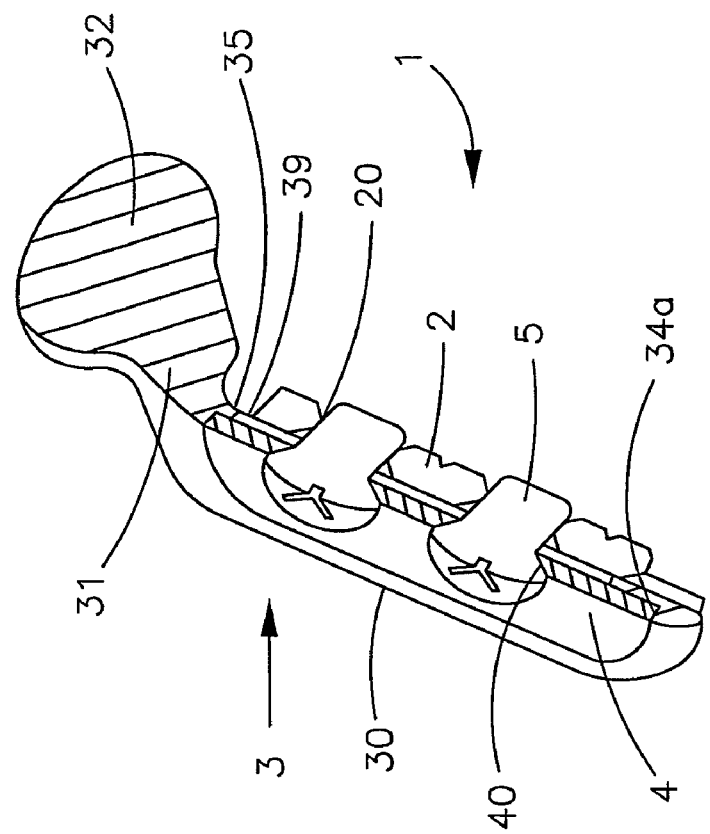
FIG. 5B shows a cross-sectional view of an exemplary condylar-head replacement attached to a reconstruction plate.
Figure 5A:
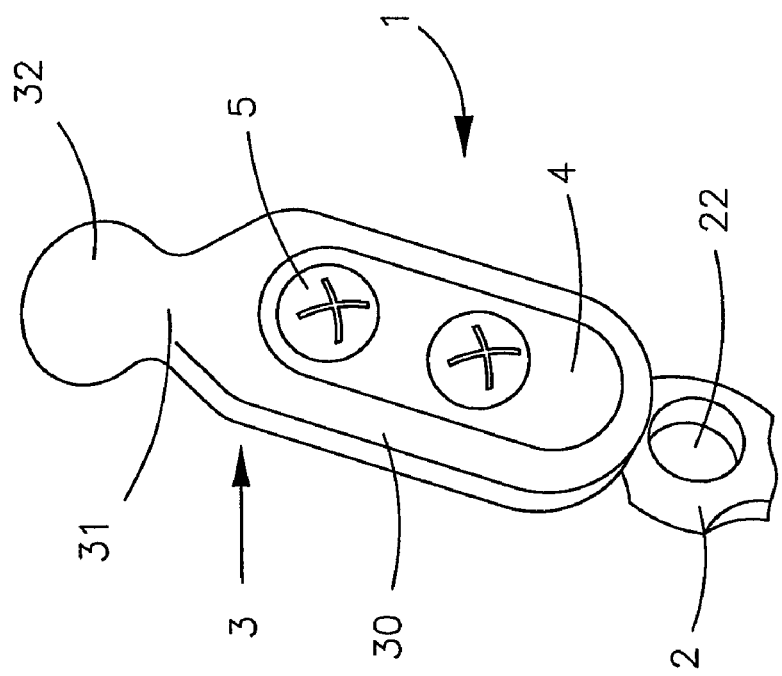
FIG. 5A shows an exemplary condylar-head replacement attached to a reconstruction plate.

FIGS. 5A and 5B show the assembly of a condylar-head replacement 1 on a reconstruction plate 2 according to a preferred embodiment of the invention. As shown, the medial side 39 of the primary attachment plate 30 may be positioned over a lateral side of the reconstruction plate 2, such that the reconstruction plate 2 is disposed inside the recessed channel 35 and the slot 33 is aligned over the holes 22 in the reconstruction plate 2. A height-adjustment plate 4 corresponding to a desired condylar-head height may be positioned over the slot 33 and in the recess 34a of the primary attachment plate 30, such that the holes 40 in the height-adjustment plate 4 are aligned over the slot 33 in the primary attachment plate 30 and the holes 22 in the reconstruction plate 2. As shown, conventional fasteners, such as screws 5 for example, may be used to fasten the condylar-head attachment 3 to a reconstruction plate 2 by driving the screws 5 through holes 40 of the height-adjustment plate 4, slot 33 of the primary attachment plate 30, and holes 22 of the reconstruction plate 2. Preferably, the heads of the screws 5 rest inside the countersinks 41 of the height-adjustment plate 4 such that the heads of the screws are below or flush with the surface of the height adjustment plate 4.

Figure 6:
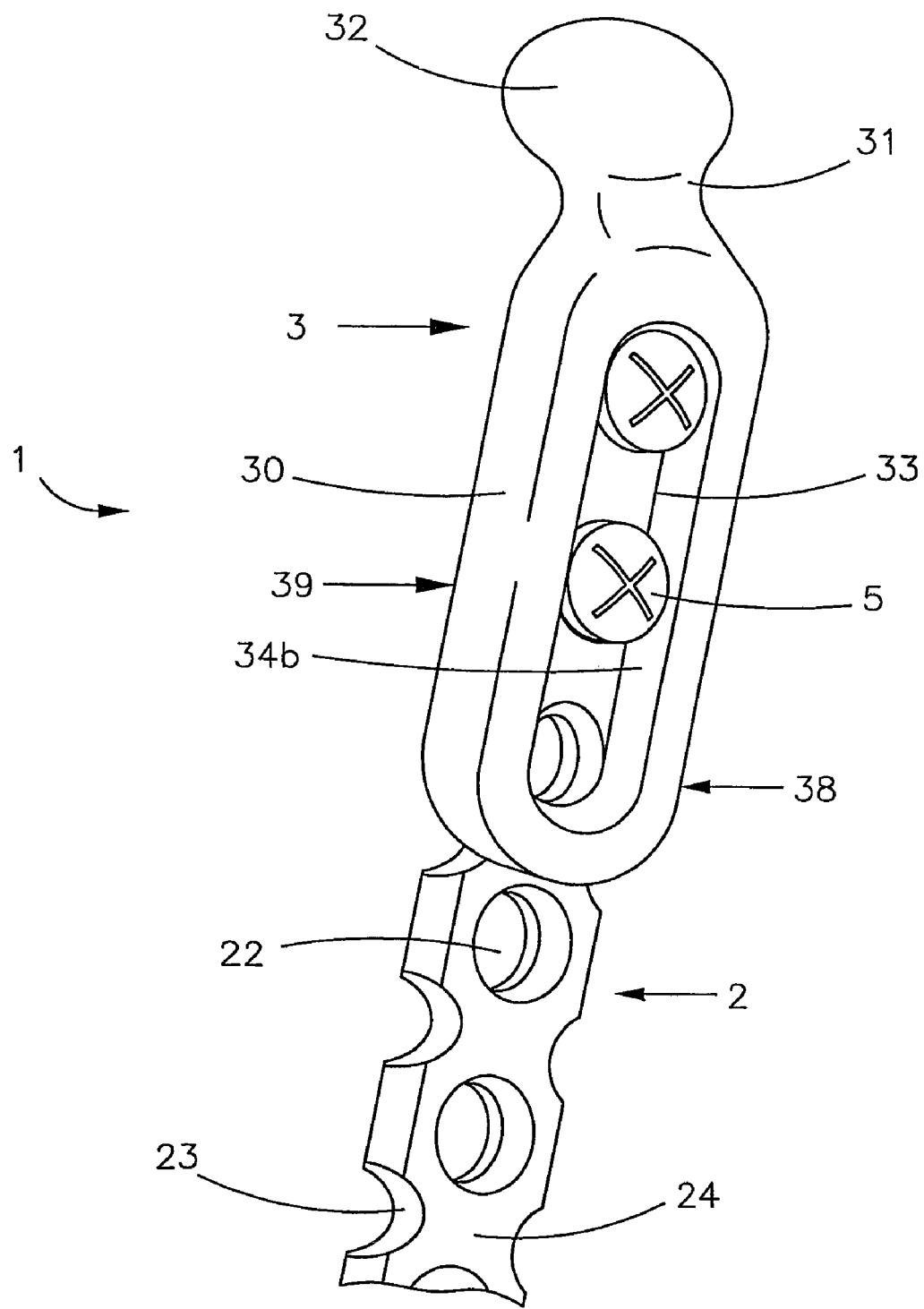
FIG. 6 shows another exemplary condylar-head replacement attached to a reconstruction plate.

FIG. 6 shows a condylar-head replacement 1 according to another embodiment. In this embodiment, the condylar-head replacement 1 includes a condylar head attachment 3, screws 5, a reconstruction plate 2, and does not include a height-adjustment plate 4. As shown, the medial side 39 of the primary attachment plate 30 may be positioned over a lateral side of the reconstruction plate 2, such that the reconstruction plate 2 is disposed inside the recessed channel 35 and the slot 33 is aligned over the holes 22 in the reconstruction plate 2. The condylar-head attachment 3 may be slidably adjusted with respect to the reconstruction plate 2 to a desired condylar-head height. In order to secure the condylar-head attachment 3 to the reconstruction plate 2, screws 5 are driven through the slot 33 in the primary attachment plate 30 and into the holes 22 in the reconstruction plate 2 such that the heads of the screws 5 rest in the recess 34b in the primary attachment plate 30. The width of recess 34b may be narrower than the width of recess 34a as shown in FIGS. 3A-3E, because recess 34b only needs to accommodate a screw 5 and does not have to accommodate a height-adjustment plate 4 as does recess 34a.

FIG. 7A-7D show yet another embodiment of the condylar-head replacement 1 adjusted to different condylar-head heights. As shown the condylar-head replacement 1 includes a reconstruction plate 2, a condylar-head attachment 3, a secondary attachment plate 6, bolts 7, and screws 5.

FIGS. 8A and 8B show an exemplary condylar-head attachment 3 according to the embodiment of FIGS. 7A-7D. As shown, the condylar-head attachment 3 includes a primary attachment plate 30, a neck 31, and a condylar head 32. Also shown is a slot 33 cutout in the center of the primary attachment plate 30 along the longitudinal direction. As shown in FIG. 8B, a recess 34b may be formed on the lateral side 38 of the primary attachment plate 30 extending concentrically around the slot 33. As shown in FIG. 8A, a recessed channel 35 may be formed on the medial side 39 of the primary attachment plate 30 and may extend around the slot 33 from proximate the neck 31 to the bottom of the primary attachment plate 30. Recessed channel 35 is preferably open at the bottom end to receive a reconstruction plate 2. As shown, the recessed channel 35 may have a substantially rectangular shape. As shown in FIG. 8A, the medial side 39 of the primary attachment plate 30 may also include a series of mortises 36 and tenons 37 adjacent to each of the longitudinal edges of the recessed channel 35.

Figure 9B:
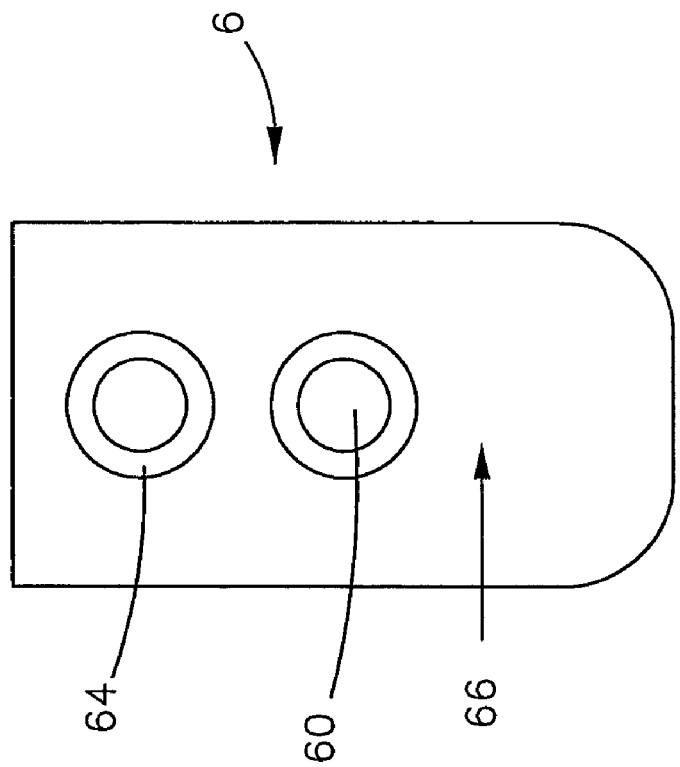
FIG. 9B shows a view of the medial side of the exemplary secondary attachment plate of FIG. 9A.
Figure 9A:
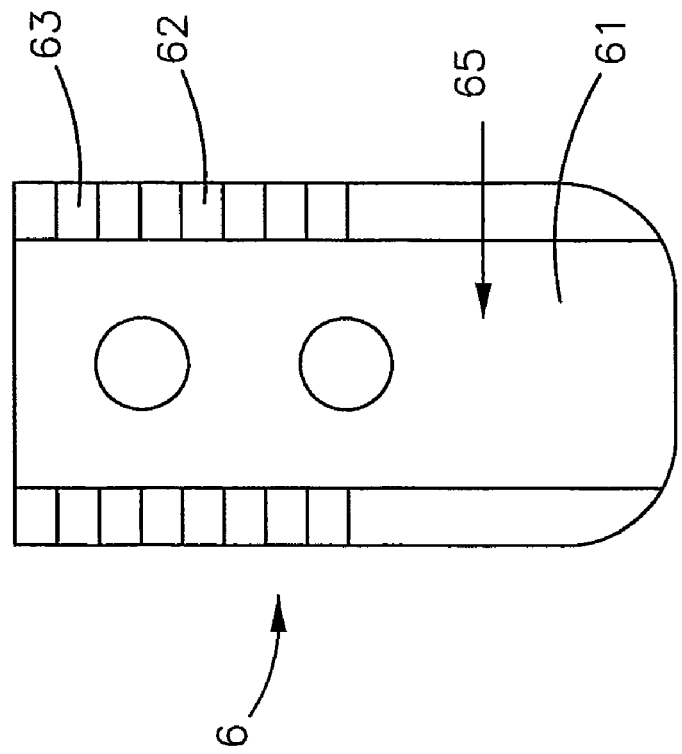
FIG. 9A shows a view of the lateral side of an exemplary secondary attachment plate.

FIGS. 9A and 9B show an exemplary secondary attachment plate 6 according to the embodiment of FIGS. 7A-7D. As shown, the secondary attachment plate 6 may include at least one hole 60 aligned along a longitudinal midline of the plate 6, but preferably at least two holes 60. As shown in FIG. 9A, a rectangular recessed channel 61 may be formed on the lateral side 65 of the secondary attachment plate 6 that extends from the top to the bottom. The holes 60 are preferably disposed along a midline of the recessed channel 61 and are spaced apart substantially the same distance as the holes 22 in a complementary reconstruction plate 2. As shown in FIG. 9B, the medial side 66 of the secondary attachment plate 6 may include countersinks 64 concentrically surrounding the holes 60. The lateral side 65 of the secondary attachment plate may also include a series of mortises 62 and tenons 63 adjacent to the longitudinal edges of the recessed channel 61. The secondary attachment plate 6 preferably includes a shape that generally corresponds to the shape of the primary attachment plate 30. As shown, the secondary attachment plate 6 may include a substantially rectangular shape.

Figure 7A:
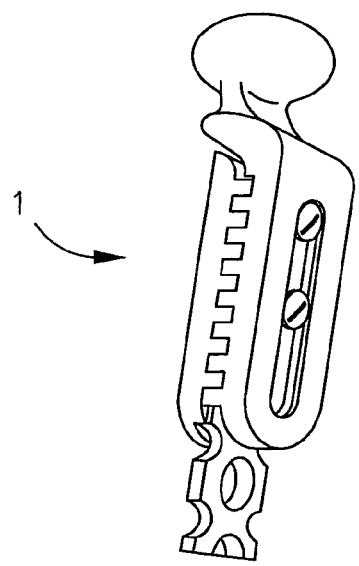
FIGS. 7A-7C show another exemplary condylar-head replacement attached to a reconstruction plate at different condylar-head heights.
Figure 7B:
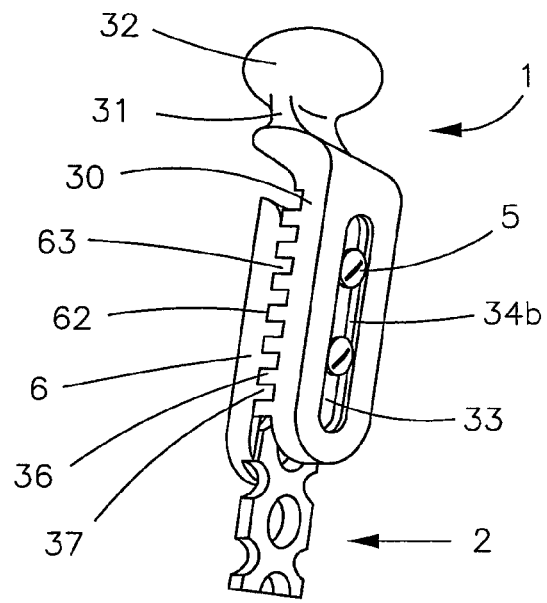
Figure 7C:
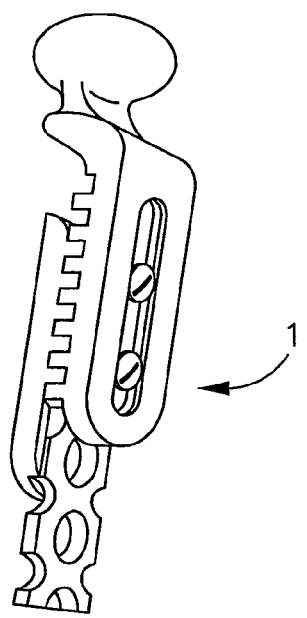

Referring back to FIGS. 7A-7D, the condylar-head replacement 1 may be assembled by disposing the reconstruction plate 2 between the medial side 39 of the primary attachment plate 30 and the lateral side 65 of secondary attachment plate 6. As shown, the holes 60 on the secondary attachment plate 6, the holes 22 on the reconstruction plate 2, and the slot 33 on the primary attachment plate 30 are aligned. In this embodiment, the reconstruction plate 2 may be disposed in a cavity formed by the recessed channels 35, 61 of the primary 30 and secondary attachment plates 6, such that the mortises 36, 62 and tenons 37, 63 on the opposing sides of the primary attachment plate 30 and the secondary attachment plate 6 engage. As shown in FIGS. 7A-7C, the condylar-head height may be adjusted by moving the condylar-head attachment 3 with respect to the secondary attachment plate 6 and the reconstruction plate 2.

Figure 7D:
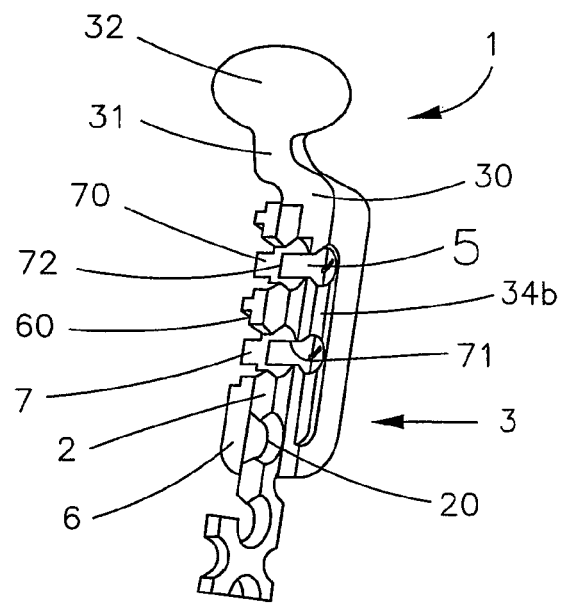
FIG. 7D shows a cross-sectional view of the exemplary condylar-head replacement of FIGS. 7A-7C.

Referring to FIG. 7D, the secondary attachment plate 6 may be secured to the reconstruction plate 2 with bolts 7 by placing the bolts 7 through the holes 60 in the secondary attachment plate 6 and into the holes 22 in the reconstruction plate 2. As shown, the bolts 7 may have a head 70, a tip opening 71, and tubular cavity 72 extending from proximate the head 70 to the tip opening 71. As, shown, screws 5 may be used to secure the primary attachment plate 30 to the reconstruction plate 2 by driving the screws 5 through the slot 33 in the primary attachment plate 30 and into the cavity 72 of the bolts 7 that secure the secondary attachment plate 6 to the reconstruction plate 2. In an alternative embodiment, the primary attachment plate 30 and the secondary attachment plate 6 may be secured to the reconstruction plate 2 without the use of bolts 7. For example, screws 5 are driven through the slot 33 in the primary attachment plate 30, through the holes 22 in the reconstruction plate 2, and into the holes 60 in the secondary attachment plate 6. The primary attachment plate 30, the secondary attachment plate 6, and the reconstruction plate 2 may be fastened together using any suitable means.

According to another aspect to the invention, the condylar-head replacement 1 is preferably used as a temporary implant for the reconstruction of the mandible after resection of the condyloid process until a definitive and more permanent reconstructive procedure can be performed. The condylar-head replacement 1 of the present invention obviates the need for custom fabrication of a condylar-head replacement for a patient. According to the present invention, the condylar-head replacement 1 may be used with a new and/or conventional reconstruction plate 2 and may be adjusted for a particular patient. Alternatively, the condylar-head replacement 1 of the present invention may also be suitable as a permanent prosthesis for permanent reconstruction of the condyloid process.

Depending on the particular embodiment, a desired condylar-head height may be achieved by, for example: adjusting the location of the condylar-head attachment relative to the reconstruction plate; adjusting the location of the fasteners within the slot of the primary attachment plate; selecting the height-adjustment plate from a plurality of height-adjustment plates having holes corresponding to varying heights; changing the orientation of the height-adjustment plate (e.g., rotating 180 degrees); adjusting the mating of the corresponding tenons and mortises between the primary attachment plate and the secondary attachment plate; or the like. While systems and methods have been described and illustrated with reference to specific embodiments, those skilled in the art will recognize that modification and variations may be made without departing from the principles described above and set forth in the following claims. Accordingly, reference should be made to the following claims as describing the scope of disclosed embodiments.

What is claimed is:

1. A condylar-head replacement kit, comprising:
   an attachment plate;
   an elongate slot extending through said attachment plate along a longitudinal direction;
   a recess formed on a lateral side of said attachment plate, said recess extending outwardly from and circumferentially around said elongate slot;
   a neck extending from a top of said attachment plate;
   a condylar head extending from said neck; and
   a plurality of height-adjustment plates being adapted to fit over said elongate slot and in said recess of said attachment plate, each of said plurality of height-adjusting plates having at least one hole, each hole corresponding to different condylar head heights.

2. The condylar-head replacement kit of claim 1, further comprising a fastener, said fastener adapted to be inserted in said elongate slot of said attachment plate, wherein said fastener may be moved within said elongate slot to adjust a height of said condylar head.

3. The condylar-head replacement kit of claim 1, wherein the plurality of height-adjustment plates further comprise a countersink, said countersink being concentrically formed around said hole in said plurality of height-adjustment plates.

4. The condylar-head replacement kit of claim 1, wherein the plurality of height-adjustment plates further comprise an asymmetrical shape along a centerline dividing said plurality of height-adjustment plates into a top half and a bottom half.

5. The condylar-head replacement kit of claim 1, wherein the plurality of height-adjustment plates further comprise a symmetrical shape.

6. The condylar-head replacement kit of claim 1, wherein the plurality of height-adjustment plates further comprise a shape that is complementary to a shape of said recess on said attachment plate.

7. The condylar-head replacement kit of claim 1, wherein said at least one hole may be placed in different positions along a longitudinal midline of said plurality of height-adjustment plates.

8. The condylar-head replacement kit of claim 1, wherein a different position of said at least one hole along a longitudinal midline of said height-adjustment plate corresponds to a different height of said condylar head.

9. The condylar-head replacement kit of claim 1, further comprising a recessed channel formed on a medial side of said attachment plate, said recessed channel surrounding said elongate slot.

10. The condylar-head replacement kit of claim 9, wherein the recessed channel further comprises an open bottom end.

11. The condylar-head replacement kit of claim 1, wherein the attachment plate carries at least one hole that corresponds to a particular height of said condylar head.

12. The condylar-head replacement kit of claim 11, wherein the at least one hole is defined by one of the plurality of height-adjustment plates configured to be carried by the attachment plate.

13. The condylar-head replacement kit of claim 1, wherein the recess is enclosed.

14. A condylar-head replacement kit, comprising:
   an attachment plate;
   an elongate slot extending through said attachment plate along a longitudinal direction;
   a neck extending from a top of said attachment plate;
   a condylar head extending from said neck;
   a plurality of height-adjustment plates configured to fit over said elongate slot, the plurality of height-adjustment plates having a pair of openings extending therethrough, wherein the openings are aligned with the elongate slot when the plurality of height-adjustment plates are fit over said elongated slot, each of the plurality of height-adjustment plates is shaped differently to correspond to different condylar head heights; and
   a pair of fasteners configured to be inserted through said openings and through said elongate slot so as to attach the attachment plate to a reconstruction plate.

15. The condylar-head replacement kit of claim 14, wherein the shape comprises a spacing of openings.

16. The condylar-head replacement kit of claim 14, further comprising a recess formed on a lateral side of said attachment plate, said recess extending outwardly from and circumferentially around said slot.

17. The condylar-head replacement kit of claim 16, further comprising a plurality of height-adjustment plates shaped such that they fit over said elongate slot and in said recess of said attachment plate, said plurality of height-adjustment plates having at least one hole.

18. The condylar-head replacement kit of claim 14, further comprising a recessed channel formed on a medial side of said attachment plate, said recessed channel surrounding said elongate slot and having an open bottom end; wherein the channel is configured to receive the reconstruction plate therein.

19. The condylar-head replacement kit of claim 14, further comprising a wall that defines a recess, said recess formed on a lateral side of said attachment plate and extending outwardly from said elongate slot, wherein the wall is configured to engage the plurality of height-adjustment plates so as to ensure that the openings are aligned with the elongate slot.

20. A condylar-head replacement kit, comprising:
   an attachment plate including a neck and a condylar head extending from said neck, and an elongate slot;
   a plurality of height-adjustment plates configured to attach to the attachment plate;
   wherein each of said plurality of height-adjustment plates comprises at least one screw hole, and the at least one screw hole of at least a first one of the plurality of height-adjustment plates is differently arranged with respect to the at least one screw hole of at least a second one of the plurality of height-adjustment plates, such that when the first and second height adjustment plates are disposed in the slot, the respective at least one screw holes are positioned at different locations corresponding to a different condylar head heights.

21. The condylar-head replacement kit of claim 20, wherein the at least one hole comprises two holes.

22. The condylar-head replacement kit of claim 20, wherein each of the at least one holes corresponds to a different condylar head height.

23. The condylar-head replacement kit of claim 20, wherein the at least one hole may be placed in different positions along a longitudinal midline of the plurality of height-adjustment plates.

* * * * *